United States Patent [19]
Mutterer

[11] 3,974,166
[45] Aug. 10, 1976

[54] PROCESS FOR THE MANUFACTURE OF BROMOPYRIDINES

[75] Inventor: Francis Mutterer, St. Louis, France

[73] Assignee: Ciba-Geigy Corporation, Ardsley, N.Y.

[22] Filed: June 17, 1974

[21] Appl. No.: 479,920

[30] Foreign Application Priority Data
July 10, 1973 Switzerland.................... 10020/73

[52] U.S. Cl.................. 260/290 HL; 260/295.5 R;
260/296 R; 260/297 R; 71/94
[51] Int. Cl.$^2$............... C07D 213/26; C07D 213/48;
C07D 213/61; C07D 213/02
[58] Field of Search............ 260/290, 295.5, 296 R, 260/296

[56] References Cited
UNITED STATES PATENTS

| | | | |
|---|---|---|---|
| 3,694,332 | 9/1972 | Parker | 260/290 |
| 3,809,695 | 5/1974 | Steinmetz et al. | 260/290 |
| 3,849,422 | 11/1974 | Weis | 260/290 |

FOREIGN PATENTS OR APPLICATIONS

| | | | |
|---|---|---|---|
| 2,314,664 | 10/1973 | Germany | 260/290 |
| 1,038,530 | 8/1966 | United Kingdom | 260/290 |

OTHER PUBLICATIONS

Klingsberg, Heterocyclic Compounds, Pyridine and Derivatives, part 2, p. 341, (1961).
Palmer, Heterocyclic Compounds, p. 40, (1967).
Hertog, Chem. Abstracts, vol. 46, col. 8654i–55a–b, (1952).

*Primary Examiner*—Harry I. Moatz
*Attorney, Agent, or Firm*—Luther A. R. Hall

[57] ABSTRACT

A novel process for the preparation of 2,4-dibromo-, 2,6-dibromo- and 2,4,6-tribromopyridines, and the new bromopyridines to be obtained therewith, are disclosed. The novel process comprises treating 2,4-dichloro-, 2,6-dichloro- and 2,4,6-trichloropyridines, in an anhydrous organic medium, with gaseous HBr at temperatures between 80° and 130°C, said process being both simple and economical.

2 Claims, No Drawings

PROCESS FOR THE MANUFACTURE OF BROMOPYRIDINES

The present invention relates to a new process for the manufacture of bromopyridines, the new bromopyridines which can be obtained thereby, the use of the new bromopyridines in plant protection, for example as active compounds for combatting phytopathogenic fungi, and the agents which contain the new active compounds.

Hitherto, bromopyridines have only been accessible to a limited extent. Certain bromopyridines can be prepared by means of a substitution reaction by treating nitropyridines, such as 3,5-diethoxy-2,6-dinitropyridine and 2-nitro-3,5-diethoxypyridine, with 30 – 40% strength solutions of hydrogen bromide in anhydrous acetic acid. The reaction is carried out with advantage in a closed system at temperatures between about 100° and 130°C. A chlorine/bromine transhalogenation has hitherto only been known in the case of certain other nitrogen heterocyclic compounds: 2-(o-alkoxyphenyl)-4,6-dichlorotriazines can be converted in solution in o-dichlorobenzene by means of hydrogen bromide gas into 2-(o-hydroxyphenyl)-4,6-dibromotriazine. 5-Chloro-7-bromo-isatin can be obtained by treating 5,7-dichloro-isatin with aqueous potassium bromide solution and a little concentrated sulphuric acid at 60°C. Finally, the bromination of 4,6-dichloro-2,5-dimethylpyrimidine with $Br_2$ gives 4-bromo-5-bromomethyl-6-chloro-2-methylpyrimidine.

It has now been found that 2,4-dibromopyridines, 2,6-dibromopyridines and 2,4,6-tribromopyridines, optionally containing further substituents, can be prepared in a simple and economical manner and with high yields by treating 2,4-dichloropyridines, 2,6-dichloropyridines or 2,4,6-trichloropyridines, optionally containing further substituents, with hydrogen bromide gas in an anhydrous organic medium at temperatures between 80° and 130°C.

Depending on the number of chlorine atoms present in the 2-, 4- and/or 6-position, the starting products which can be employed in the process according to the invention can contain 2 or 3 further ring-substituents.

Possible additional ring-substituents are any desired groups which are stable under the reaction conditions, for example amino radicals and N-alkylamino, N,N-dialkylamino and alkyl radicals with 1 to 18, especially 1 to 4, carbon atoms in the alkyl part; phenyl radicals and halogenophenyl radicals, especially chlorophenyl or fluorophenyl radicals, and alkylphenyl radicals with 1 to 4 carbon atoms in the alkyl radical; and naphthyl radicals or phenoxy radicals. The starting pyridines preferably contain, as additional substituents, electron-attracting substituents, such as halogen atoms, particularly chlorine atoms, or chloromethyl, trichloromethyl, trifluoromethyl, nitro, aldehyde or carboxyl radicals, since the transhalogenation generally takes place more rapidly in the case of chloropyridines which are substituted in this way.

The chloropyridine starting products according to the definition are known or can be prepared by methods which are in themselves known. Examples of suitable starting products are:
2,4-dichloropyridine,
2,6-dichloropyridine,
2,4-dichloro-6-trichloromethylpyridine,
2,4-dichloro-5-amino-pyridine,
2,6-dichloro-4-nitropyridine,
2,6-dichloro-3-chloromethylpyridine,
2,6-dichloro-3-nitropyridine,
2,6-dichloro-3-chloromethyl-5-nitropyridine,
2,6-dichloropyridine-3-aldehyde,
2,6-dichloronicotinic acid,
2,6-dichloro-3-trifluoromethylpyridine,
2,4-dichloro-3-nitro-6-n-propylpyridine,
2,3,6-trichloropyridine,
2,5,6-trichloro-3-chloromethylpyridine,
2,5,6-trichloro-3-aminopyridine,
2,5,6-trichloro-3-nitropyridine,
2,5,6-trichloropyridine-3-aldehyde,
2,5,6-trichloronicotinic acid,
2,3,4,5-tetrachloropyridine,
2,3,5,6-tetrachloropyridine,
2,3,4,5-tetrachloro-6-phenylpyridine,
2,3,4,5-tetrachloro-6-(1-naphthyl)-pyridine,
2,3,4,5-tetrachloro-6trichloromethylpyridine,
2,3,4,5-tetrachloro-6-p-fluorophenylpyridine and
2,3,4,5,6-pentachloropyridine.

The process according to the invention is particularly suitable for the manufacture of bromopyridines of the formula I

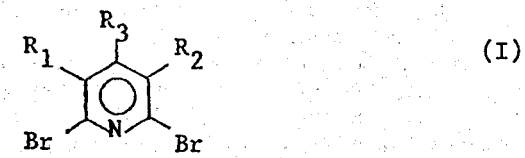

wherein $R_1$ represents hydrogen, a chlorine atom or the nitro group, $R_2$ represents hydrogen, a chlorine atom, —CHO, —COOH, —CH$_2$Br or the amino, nitro or trifluoromethyl group, and $R_3$ represents hydrogen or a bromine atom, using as starting products chloropyridines of the formula II

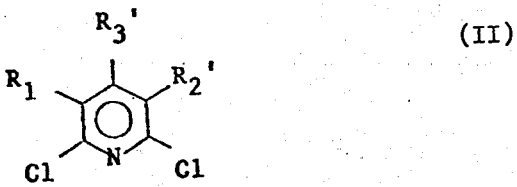

wherein $R_1$ has the meaning indicated under formula I, $R_2'$ represents hydrogen, a chlorine atom, —CHO, —COOH, —CH$_2$Cl or the amino, nitro or trifluoromethyl group, and $R_3'$ represents hydrogen or a chlorine atom.

By means of the process according to the invention it is also possible to manufacture, inter alia, new bromopyridines of the formula III

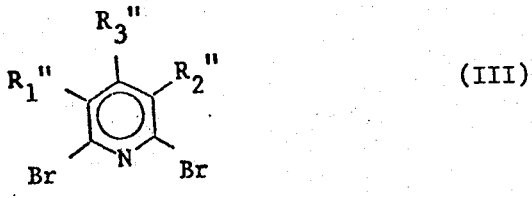

wherein $R_1''$ represents hydrogen or a chlorine atom, $R_2''$ represents a chlorine atom or the nitro or trifluoromethyl group, and $R_3''$ represents hydrogen or a bromine atom, or R₁'' represents a chlorine atom or the nitro group and also, if R₂'' denotes —COOH, represents hydrogen, R₂'' represents —CH₂Br or —COOH, and R₃'' represents hydrogen.

These new bromopyridines are valuable active compounds for plant protection.

Examples of suitable organic solvents for carrying out the process according to the invention are chlorobenzene, dichlorobenzenes, toluene and xylenes. The reaction is preferably carried out in anhydrous acetic acid.

The reaction temperatures are preferably between 100° and 110°C. The reaction times are generally about 2 to 20 hours.

The reaction is suitably carried out in an open system with the continuous introduction of hydrogen bromide gas into the anhydrous organic medium containing the starting product.

After the completion of the reaction, the bromopyridines can be isolated in the usual manner and, if appropriate, can be purified, for example by precipitation onto ice, filtering off and drying. End products which are sensitive to hydrolysis, such as 2,6-dibromonicotinic acid and 2,6-dibromo-5-chloronicotinic acid, are suitably isolated by removing the organic solvent and the hydrogen bromide gas in vacuo and recrystallising the residue from water or a suitable solvent, such as ethanol, benzene, toluene or xylenes.

In general, the bromopyridines are produced in a state of very high purity and in good to very good yields. They are white to yellowish-white crystalline substances which are soluble in numerous organic solvents, such as chloroform, methylene chloride, methanol, ethanol, acetone, hexane, cyclohexane, benzene, N,N-dimethylformamide, dimethylsulphoxide or diethyl ether.

It is surprising that functional groups present on the pyridine ring, such as —NO₂, —CHO and —COOH groups, are stable under the reaction conditions according to the invention.

EXAMPLE 1

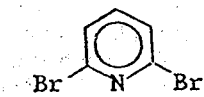

7.4 g. (0.05 mol) of 2,6-dichloropyridine are admixed with 100 ml of anhydrous acetic acid. The reaction mixture is then heated to 110°C with exclusion of moisture. Hydrogen bromide gas is passed in continuously at this temperature for 9 hours while stirring the reaction mixture. The reaction product is then precipitated by pouring the reaction mixture onto ice, and is filtered off, washed with water and dried. 10.9 g (92% of theory) of 2,6-dibromopyridine, melting point 115°C, are obtained.

Analysis for C₅H₃NBr₂ (molecular weight 237): calculated C 25.34% H 1.28% N 5.91% Br 67.43% Cl -
found C 25.3% H 1.4% N 5.9% Br 67.4% Cl<0.3
Both 2,6-dichloropyridine and 2,6-dibromopyridine are known.

EXAMPLES 2 – 15

The table which follows lists further bromopyridines which have been prepared by the process described in Example 1. In the case of Examples 12 and 13, the reaction product was isolated by removing the acetic acid and the hydrogen bromide in vacuo and recrystallising the dry residue from water.

Table

| Ex. No. | Chloropyridine of the formula II | Bromopyridine of the formula I | Reaction time/temperature | Yield % of theory | Melting point °C | | C | H | Analysis % N | Cl | Br |
|---|---|---|---|---|---|---|---|---|---|---|---|
| 2 | (2,3-dichloro) | (2,3-dibromo) | 14 hours at 110°C | 93 | 70–72 | Calculated<br>Found | 21.10<br>22.05 | 0.75<br>0.76 | 5.16<br>5.08 | 13.05<br>15.18 | 58.60<br>56.81 |
| 3 | (2,3,5-trichloro) | (2,3,5-tribromo) | 12 hours at 110°C | 92 | 93–95 | Calculated<br>Found | 19.63<br>18.4 | 0.33<br>0.4 | 4.58<br>4.4 | 23.17<br>24.0 | 52.23<br>51.2 |
| 4 | (2,3,4,5-tetrachloro) | (2,3,4,5-tetrabromo) | 21 hours at 110°C | 72 | 198–202 | Calculated<br>Found | 15.61<br>15.68 | —<br>— | 3.64<br>3.68 | 18.44<br>18.64 | 62.32<br>62.10 |
| 5 | 2-chloro-3-chloromethyl | 2-bromo-3-bromomethyl | 7 hours at 110°C | 95 | 99–101 | Calculated<br>Found | 21.84<br>21.95 | 1.22<br>1.27 | 4.24<br>4.34 | —<br><0.3 | 72.64<br>72.55 |
| 6 | 2,6-dichloro-3-chloromethyl | 2,6-dibromo-3-bromomethyl | 11 hours at 110°C | 94 | 73–75 | Calculated<br>Found | 19.78<br>19.89 | 0.83<br>0.86 | 3.85<br>3.99 | 9.73<br>10.00 | 65.70<br>65.30 |

Table-continued

| Ex. No. | Chloropyridine of the formula II | Bromopyridine of the formula I | Reaction time/ temperature | Yield % of theory | Melting point °C | | C | H | Analysis % N | Cl | Br |
|---|---|---|---|---|---|---|---|---|---|---|---|
| 7 | (structure: pyridine with NO₂, Cl, Cl) | (structure: pyridine with NO₂, Br, Br) | 4 hours at 80°C | 82 | 78 | Calculated<br>Found | 21.30<br>21.54 | 0.71<br>0.68 | 9.93<br>9.96 | —<br><0.3 | 56.67<br>56.60 |
| 8 | (structure: Cl, NO₂, Cl, Cl pyridine) | (structure: Cl, NO₂, Br, Br pyridine) | 4 hours at 80°C | 92 | 87–89 | Calculated<br>Found | 18.99<br>19.19 | 0.32<br>0.33 | 8.86<br>8.74 | 11.21<br>11.31 | 50.53<br>50.97 |
| 9 | (structure: O₂N, CH₂Cl, Cl, Cl pyridine) | (structure: O₂N, CH₂Br, Br, Br pyridine) | 6 hours at 110°C | 98 | 72–76 | Calculated<br>Found | 19.22<br>19.8 | 0.81<br>0.9 | 7.47<br>7.2 | —<br><0.3 | 63.93<br>65.2 |
| 10 | (structure: CHO, Cl, Cl pyridine) | (structure: CHO, Br, Br pyridine) | 1.5 hours at 110°C | 87 | 125–127 | Calculated<br>Found | 27.21<br>27.08 | 1.14<br>1.11 | 5.29<br>5.31 | —<br><0.3 | 60.33<br>60.27 |
| 11 | (structure: Cl, CHO, Cl, Cl pyridine) | (structure: Cl, CHO, Br, Br pyridine) | 6 hours at 110°C | 88 | 118–122 | Calculated<br>Found | 24.07<br>24.1 | 0.67<br>0.7 | 4.84<br>4.7 | 11.84<br>12.4 | 53.38<br>53.1 |
| 12 | (structure: COOH, Cl, Cl pyridine) | (structure: COOH, Br, Br pyridine) | 6 hours at 110°C | 78 | 150 | Calculated<br>Found | 25.65<br>25.44 | 1.08<br>1.02 | 4.98<br>4.98 | —<br><0.3 | 56.87<br>57.17 |
| 13 | (structure: Cl, COOH, Cl, Cl pyridine) | (structure: Cl, COOH, Br, Br pyridine) | 6 hours at 110°C | 82.5 | 166 | Calculated<br>Found | 22.88<br>22.9 | 0.64<br>0.8 | 4.45<br>4.5 | 11.23<br>11.4 | 50.74<br>50.6 |
| 14 | (structure: CF₃, Cl, Cl pyridine) | (structure: CF₃, Br, Br pyridine) | 4.5 hours at 120°C | 83 | Boiling point °C 99/12 mm Hg | Calculated<br>Found | 23.64<br>23.8 | 0.66<br>0.8 | 4.59<br>5.0 | —<br>— | 52.41<br>52.3 |
| 15 | (structure: Cl, NH₂, Cl, Cl pyridine) | *) (structure: Cl, NH₂, Br, Br pyridine) | 12 hours at 110°C | 70.2 | 175 | Calculated<br>Found | 20.97<br>22.6 | 1.06<br>1.3 | 9.78<br>10.0 | 12.38<br>12.3 | 55.79<br>52.3 |

*) Contaminated by a little N-acylated product.

The starting products used in Examples 1 – 4, 7 and 12 are known. The remaining chloropyridines can be prepared as follows:

2,6-Dichloro-3-chloromethylpyridine (Example 5)

588 g (3 mols) of 3-chloro-3-chloromethylglutarimide (obtained by chlorinating α-methyleneglutaronitrile with the formation of 1,2-dichloro-2,4-dicyanobutane and subsequently cyclising the latter to give 3-chloro-3-chloromethylglutarimide by methods which are in themselves known) and 3 l of phosphorus oxychloride are charged into a 6 l tantalum autoclave and are heated at 160°C for 3 hours. The resulting brown solution is then freed from phosphorus oxychloride on a rotary evaporator and the black, oily residue is poured, while still hot, into a mixture of approx. 3 liters of ice and water. The ice/water mixture is stirred for aprox. 4 hours, until a light brown suspension of crystals has been formed. The crystals are filtered off with suction and are washed several times with water. The crystals are then filtered off again and are dried in a vacuum drying cabinet at 25°C over diphosphorus pentoxide.

2,5,6-Trichloro-3-chloromethylpyridine (Example 6)

82.8 g (0.333 mol) of 3,5,6-trichloro-3-chloromethyl-5,6-dehydro-piperidon-2-one (obtained by reacting 3-chloro-3-chloromethylglutarimide with phosphorus pentachloride at a temperature of 70° – 71°C) and 400 ml (4.4 mols) of phosphorus oxychloride are heated in an autoclave at 180°C for 3 hours. Excess phosphorus oxychloride is then removed from the reaction solution on a rotary evaporator and the dark brown residue is poured onto ice. The crystals precipitated are filered off with suction, washed with water and dried overnight over diphosphorus pentoxide.

2,5,6-Trichloro-3-nitropyridine (Example 8)

3.6 g. (0.02 mol) of 2,5,6-trichloropyridine are dissolved in a mixture of 20 ml of 100% strength fuming nitric acid and 16 ml of concentrated sulphuric acid and are then heated at 100°C in an oil bath for 12 hours. After cooling to approx. 20°C, the reaction mixture is poured onto ice. The crude product is produced in the form of slightly yellowish crystals, which are filtered off with suction, washed with water and dried at 30°C in vacuo over KOH. 3 g (66.7% of theory) of 2,5,6-trichloro-3-nitropyridine are obtained in the form of crystals which, after sublimation at 30° – 40°C/12 mm Hg. melt at 68° – 70°C.

Analysis for $C_5HCl_3N_2O_2$ (molecular weight 227.4): calculated C 26.41% H 0.44% Cl 46.77% N 12.32% found C 26.2% H 0.5% Cl 47.0% N 12.2%

2,6-Dichloro-3-chloromethyl-5-nitropyridine (Example 9)

117.5 g (0.6 mol) of 2,6-dichloro-3-chloromethylpyridine are dissoled in a mixture of 540 ml of concentrated sulphuric acid and 600 ml of 100% strength fuming nitric acid. The reaction mixture is then heated at 110°C in an oil bath for 5 hours. After cooling to approx. 20°C, the reaction mixture is poured onto ice. The resulting crystals are filtered off and are purified by being well ground with water in a mortar and then filtered off with suction and rinsed with water on the filter. After drying the crude product in vacuo at 25°C over diphosphorus pentoxide. crude 2,6-dichloro-3-chloromethyl-5-nitropyridine is obtained in the form of pale yellow crystals, which can be recrystallised from methanol.

2,6-Dichloropyridine-3-aldehyde (Example 10)

840 g (4.28 mols) of 2,6-dichloro-3-chloromethylpyridine, 700 g (8.5mols) of sodium acetate and 1,600 ml of anhydrous acetic acid are heated together for 4 hours under reflux. The reaction product is then freed from solvent by distilling the latter off, is made alkaline (pH 8–10) with aqueous sodium hydroxide solution and is suspended in water. The reaction product is extracted with diethyl ether and the organic phase is dried over magnesium sulphate and evaporated. After distilling the crude product, colourless 2,6-dichloro-3-acetoxymethylpyridine is obtained.

260 g (1.18 mols) of this 2,6-dichloro-3-acetoxymethylpyridine, 520 ml (2 mols) of aqueous 2N sodium hydroxide solution and 520 ml of methanol are heated under reflux for 2 hours. The methanol is then removed on a rotary evaporator and the residual water phase is extracted by shaking with diethyl ether. After drying the organic phase over magnesium sulphate and concentrating the solution, crude crystalline 2,6-dichloro-3-hydroxymethylpyridine is obtained, which can be purified by recrystallisation from a mixture of cyclohexane/diethyl ether.

180 g (1.01 mols) of 2,6-dichloro-3-hydroxymethylpyridine are then heated under reflux for 2 hours with 600 g (6.9 mols) of manganese dioxide in 4 l of benzene. The reaction mixture is filtered while still hot and the benzene is evaporated.

After drying the residue in a vacuum drying cabinet, 2,6-dichloropyridine-3-aldehyde is obtained.

2,5,6-Trichloropyridine-3-aldehyde (Example 11)

Obtained analogously to the process described for 2,6-dichloropyridine-3-aldehyde, using 2,5,6-trichloro-3-chloromethylpyridine instead of 2,6-dichloro-3-chloromethylpyridine.

2,5,6-Trichloronicotinic acid (Example 13)

115.5 g (0.5 mol) of 2,5,6-trichloro-3-chloromethylpyridine, 500 g of 97% strength sulphuric acid, 5 g of $Hg(NO_3)_2$ and 2.5 g of $CuSO_4.5H_2O$ are charged in a sulphonation flask and are heated to 110°C in an oil bath with vigorous stirring. 150 ml (230 g) of fuming nitric acid are then added dropwise over the course of 1.5 hours. After about 50 to 60 minutes the reaction becomes exothermic. As soon as the internal temperature has reached 120°C, the oil bath is removed and is replaced by ice water cooling of such a kind that the internal temperature does not exceed 130° – 140°C. After the completion of the addition of $HNO_3$, the reaction solution is cooled to 40°C and poured onto ice. The acid precipitated is filtered off with suction, pressed well and dried in a vacuum drying cabinet at 40°C. Pure 2,5,6-trichloronicotinic acid is obtained by recrystallising the crude product from water.

2,6-Dichloro-3-trifluoromethylpyridine (Example 14)

266 g (1 mol) of 2,6-dichloro-3-trichloromethylpyridine, obtained by chlorinating 2,6-dichloro-3-chloromethylpyridine with $Cl_2$ under irradiation with UV light, and 5 g of antimony trifluoride are mixed and are heated under gentle reflux in a three-necked flask with an upright condenser (internal temperature of the melt 240°C). Portions of 10 g each of antimony trifluoride are added at intervals of 10 minutes each, up to a total quantity of 191 g (1.065 mols). The reaction mixture is then heated under reflux for a further 15 minutes and then the reflux condenser is replaced by a fractionating column and the resulting trifluoromethyl compound is distilled off at normal pressure. The distillate is diluted with 2 l of diethyl ether and the ethereal solution is washed with a solution of 1 kg of tartaric acid in 4 l of water. After distilling off the diethyl ether, 162 g of crude 2,6-dichloro-3-trifluoromethylpyridine are obtained, which, on distillation at 68° – 71°C/12 mm Hg, gives 138.4 g (64% of theory) of pure 2,6-dichloro-3-trifluoromethylpyridine.

Analysis for $C_6H_2Cl_2F_3N$ (molecular weight 216.0): calculated C 33.36% H 0.93% Cl 32.83% F 26.39% N 6.48% found C 33.6% H 1.07% Cl 33.2% F 25.98% N 6.75%

2,5,6-Trichloro-3-aminopyridine (Example 15)

2,5,6-Trichloro-3-aminopyridine is prepared in a manner which is in itself known by catalytic reduction of 2,5,6-trichloro-3-nitropyridine (compare Example 8).

The 2,6-dibromopyridines obtained in accordance with Examples 2 – 4, 6 – 9 and 12 – 15 are new.

Example 16

If Example 7 is repeated, but using 100 ml of chlorobenzene instead of the anhydrous acetic acid, the reaction to give 2,6-dibromo-3-nitropyridine is completed after about 16 hours at the same reaction temperature. Yield: 86.5% of theory.

Bromopyridines which can be obtained in accordance with the invention, especially bromopyridines of the formula I or III, can be used for plant protection. They possess, for example, good fungicidal properties, above all as a soil fungicide and seed disinfectant, against phytopathogenic fungi on various cultivated plants, such as cereals, maize, rice, vegetables, ornamental plants, varieties of fruit, vines, field crops and the like.

With these active compounds it is possible to control or destroy fungal infections occurring particularly on seeds, tubers and roots, but also on fruits, blossoms, foliage and stalks, parts of plants which grow up later then remaining protected from such infections. The application of the active compounds is carried out in the form of solid or liquid agents both on the seeds or on the above-ground parts of plants and in the soil or on the soil. Solutions or aqueous dispersions are above all suitable for the application to seeds or the above-ground parts of plants. Apart from solutions and dispersions, dusting agents, granules and sprinkling agents are also suitable for the treatment of the growth substrate (the soil).

The active compounds are especially effective against the phytopathogenic fungi belonging to the following classes, orders or species:

Smut fungi of all kinds, such as

Ustilaginales, for example, Ustilago species (*Ustilago avenae*), Tilletia species (*Tilletia tritici, Tilletia caries*), Urocystis- and Tuburcinia species, and Phoma species (*Phoma betae*).

Oomycetes, such as

Plasmodiophora species, Aphanomyces species, Pythium species, for example, Pythium debaryanum, Phytophthora species (*Phytophthora infestans, Phytophthora cactorum*), Plasmopara species (*Plasmopara viticola*), Bremia species (*Bremia lactucae*), Peronospora species (*Peronospora tabacina*) and Pseudoperonospora species (*Pseudoperonospora humuli*).

Zygomycetes, such as Rhizopus species.

Ascomycetes, such as

Eurotiales, for example, Aspergillus species, Penicillium species (*Penicillium digitatum, Penicillium italicum*), Taphrinales, for example, Taphrina species (*Taphrina deformans*), Erysiphales, for example, Erysiphes species (*Erysiphes cichoracearum, Erysiphes graminis*), Podosphaera leucotricha, Sphaerotheca species (*Sphaerotheca pannosa*), Uncinula species (*Uncinula necator*), Helotiales, such as Monilinia species (*Monilinia [Sclerotinia] fructicola, Monilinia laxa*), Diplocarpon species (*Diplocarpon rosae*), Pseudopeziza species, Sphaeriales, such as Nectria species (*Nectria galligena*), Ceratocystis species, Pseudosphaeriales, such as Venturia species (*Venturia inaequalis*), Mycosphaerella species, Ophiobolus species (*Ophiobulus graminus*), Cochliobolus species (*Helminthosporium miyabeanus*) and Cercospora species (*Cercospora beticola, Cercospora musae*).

Basidiomycetes, such as

Aphyllophorales, for example, Pellicularia species (*Pellicularia filamentora* = [*Rhizoctonia solani*]), Uredinales, for example, Puccinia species (*Puccinia triticina*), Uromyces species (*Uromyces phaseoli*), Hemileia species (*Hemileia vastatrix*), Cronartium species (*Cronartium ribicola*), Phragmidium species (*Phragmidium subcorticium*) and Gymnossporangium species.

Deuteromycetes = (Fungi imperfecti)

For example Piricularia species (*Piricularia oryzae*), Corynespora species, Thielaviopsis species, Clasterosporium species, Botrytis species (*Botrytis cinerea*), Cladosporium species, Alternaria species (*Alternaria solani*), Verticillium species (*Verticillium albo-atrum*), Phialophora species, Melanconiales, for example, Colletotrichum species, Fusarium species (*Fusarium oxysporum, Fusarium nivale*), Gloeosporium species (*Gloeosporium fructigenum*), Sphaeropsidales, for examples, Septoria species (*Septoria apicola*), Diplodia species (*Diplodia natalensis*), Mycelia sterilia, for example, Sclerotium species (*Sclerotium rolfsii*).

The bromopyridines can also be formulated with other compounds, for example other fungicides, insecticides, herbicides, bactericides, fungistatic agents, bacteriostatic agents or nematicides in various mixing ratios, mixtures of compounds being formed with advantages over the individual components. The agents according to the invention can also additionally contain plant fertilisers, trace elements and the like. Examples of products which are suitable for formulating with the bromopyridines are as follows:

dodecylguanidine acetate (Dodine),
pentachloronitrobenzene (Quintozene),
pentachlorophenol (PCP),
2-(1-methyl-n-propyl)-4,6-dinitrophenyl 2-methylcrotonate (Binapacryl),
2-(1-methyl-n-heptyl)-4,6-dinitrophenyl crotonate (Dinocap), 2,6-dichloro-4-nitroaniline (Dichloran),
2,3,4,6-tetrachloro-benzoquinone(1,4) (Chloranil),
2,3-dichloro-naphthoquinone(1,4) (Dichlone),
N-(trichloromethylthio)phthalimide (Folpet),
N-(trichloromethylthio)cyclohex-4-ene-1,2-dicarboximide (Captan),
N-(1,1,2,2-tetrachloroethylthio)cyclohex-4-ene-1,2-dicarboximide (Captafol),
N-methylsulphonyl-N-trichloromethylthio-p-chloroaniline,
N'-dichlorofluoromethylthio-N,N-dimethyl-N'-phenylsulphamide (Dichlorfluamid),
O-ethyl-S-benzyl-phenyl dithiophosphonate,
O,O-diethyl-S-benzyl-thiol phosphate,
disodium-ethylene 1,2-bis-dithiocarbamate (Nabam),
zinc-ethylene 1,2-bis-dithiocarbamate (Zineb),
manganese-(II)-ethylene 1,2-bis-dithiocarbamate (Maneb),
tetramethylthiuramdisulphide (Thiram),
1-hydroxy-3-acetyl-6-methyl-cyclohex-5-ene-2,4-dione (dehydroacetic acid),
8-hydroxyquinoline (8-Quinolinol),
2-dimethylamino-6-methyl-5-n-butyl-4-hydroxy-pyrimidine,
methyl-N-benzimidazol-2-yl N-(butylcarbamoyl)carbamate (Benomyl),
2-ethylamino-6-methyl-5-n-butyl-4-hydroxy-pyrimidine,
2,3-dicyano-1,4-dithia-anthraquinone (Dithianon),
2-(4-thiazolyl)-benzimidazole,
3,5-dimethyltetrahydro-1,3,5-thiadiazine-2-thione (Dazomet).
2,3-dihydro-5-carboxanilido-6-methyl-1,4-oxathine and pentachlorobenzyl alcohol.

The manufacture of fungicidal agents according to the invention, containing at least one new bromopyridine of the formula III, is carried out in a manner which is in itself known by intimately mixing and grinding at least one bromopyridine of the formula III with suitable carrier substances, optionally with the addition of dispersing agents or solvents which are inert towards the active compounds. The active compounds can be used for the manufacture of dusting agents, sprinkling agents, granules, sheathed granules, impregnation granules, wettable powders, pastes, emulsions, solutions or aerosols.

For the manufacture of solid processing forms (dusting agents, sprinkling agents and granules) the active compounds are mixed with solid carrier substances. The particle size of the carrier substances is appropriately up to approx. 0.1 mm for dusting agents, approx. 0.075 to 0.2 mm for sprinkling agents and 0.2 mm or greater for granules. The concentration of active substance in the solid processing forms are as a rule 0.5 to 80%. It is also possible to add to these mixtures additives which stabilise the active compound and/or nonionic, anionic and cationic substances which, for example, improve the adhesion of the active compound to plants and parts of plants (adhesives and agglutinants) and/or ensure better wettability (wetting agents) and dispersability (dispersing agents).

Concentrates of active compounds which can be dispersed in water, wettable powders, pastes and emulsion concentrates are agents which can be diluted with water to any desired concentration. They consist of active compound, carrier substance, surfaceactive substances and anti-foaming agents and, optionally, solvents. The concentration of active compound in these agents is 5 – 80%. The wettable powders and pastes are obtained by mixing and grinding the active compound with dispersing agents and with pulverulent carrier substances in suitable equipment until homogeneity is attained. In some cases it is advantageous to use mixtures of various carrier substances. Examples of suitable anti-foaming agents are silicones and the like. The active compounds are mixed, ground, sieved and liquored with the additives mentioned above in such a way that, in the case of the wettable powders, the particle size of the solid component does not exceed 0.02 to 0.04 mm and, and in the case of the pastes, does not exceed 0.03 mm. Dispersing agents, organic solvents and water are used for the manufacture of emulsion concentrates and pastes. The solvents must be virtually odourless, not phytotoxic, inert towards the active compounds and not easily combustible.

The agents according to the invention can also be used in the form of solutions. For this purpose, the active compounds are dissolved in suitable organic solvents or mixtures of solvents. The solution should contain the active compounds in a concentration range of 1 – 20%.

The following text describes processing forms of some active compounds for plant protection. If there is no indication to the contrary, parts denote parts by weight.

Dusting agents

The following materials are used for the manufacture of a 2% strength dusting agent:
2 parts of 2,6-dibromo-3-nitropyridine,
5 parts of colloidal silicic acid and
93 parts of talc.

The active compound is intimately mixed and ground with the carrier substances. The fungicidal dusting agent thus obtained is used for the treatment of seedbed soil.

Granules

The following materials are used for the manufacture of 4% strength granules:
4 parts of a 1:1 mixture of 2,6-dibromo-3,5-dichloropyridine with silicic acid,
92 parts of granulated limestone (grit),
3 parts of a mixture of 0.5 part of $C_8$–$C_9$-alkylphenoxypolyoxyethylene glycol and 2.5 parts of polyethylene glycol and
1 part of kieselguhr.

The limestone grit is impregnated with the polyethylene glycol mixture and is then mixed with the mixture of active compound and silicic acid. Kieselguhr is subsequently added as an anti-caking agent. These granules are particularly suitable for the treatment of vegetable mould.

Dry dressing agents

A dry dressing agent of the following composition is used:
20% by weight of 2,6-dibromo-3-chloropyridine,
1% by weight of paraffin oil and
79% by weight of talc.

600 g of this agent, which has a good adhesion to grains of seed, are introduced, together with 100 kg of barley seed, into a rotating drum which can be tightly sealed. The charged drum is rotated for 45 minutes; after this time virtually the whole quantity of the agent employed has become a coating on the grains of seed.

Wet treatment agents

A wet treatment agent of the following composition is used:
23.00% by weight of 2,6-dibromo-3-bromomethyl-5-nitropyridine,
1.65% by weight of alkarylpolyglycol ether (emulsifier),
1.65% by weight of $NaHSO_4.H_2O$, finely ground, and
73.70% by weight of diethyleneglycol monoethyl ether acetate.

A liquor consisting of 250 g of the above agent and 15 liters of water is prepared at room temperature; this liquor preparation is then thoroughly mixed. 100 kg of rye seed are sprayed with this aqueous preparation. The seed is then allowed to drain on a sieve and is subsequently well dried.

Wettable powders

The following constituents are used for the manufacture of (a) a 10% strength and (b) a 50% strength wettable powder:

a. 10 parts of 2,6-dibromo-3-nitro-5-chloropyridine,
1 part of the sodium salt of dibutylnaphthalenesulphonic acid,
4 parts of the calcium salt of ligninsulphonic acid,
2 parts of a mixture of Champagne-chalk and hydroxyethylcellulose (1:1),
50 parts of kaolin,
10 parts of sodium aluminium silicate and
23 parts of Champagne-chalk.

b. 50 parts of 2,6-dibromo-3-nitro-5-chloropyridine,
2 parts of octylphenoxyethylene glycol with 9 – 10 mols of ethyleneoxy groups per mol of phenol,
2 parts of a mixture of Champagne-chalk and hydroxyethylcellulose (1:1),
3 parts of heptadecyl-hydroxyethyl-imidazoline and
43 parts of kaolin.

The fungicidal effectiveness of some new active compounds of the formula III was determined by means of the following experiments:

A. Soil test 500 ppm of 2,6-dibromo-3-chloropyridine are incorporated as the active substance in dry, sterilised earth by intensive mixing. 100 cc of this earth are charged into a plastic container holding 250 cc. Approx. 10 sterilized grains of oats which are interpenetrated by fungus mycelium of the species *Fusarium oxysporum* or *Phytium debaryanum* are introduced into this container below the surface of the earth.

The earth is then moistened with 34 ml of distilled water and the container is incubated at 20° – 24°C.

After 5 days an appraisal is carried out to determine whether fungus mycelia from the grains are growing in the surrounding earth. The 2,6-dibromo-3-chloropyridine tested displayed a good action.

Good actions of a similar kind against Phytium debaryanum and/or Fusarium oxysporum are achieved using 2,6-dibromo-3,5-dichloropyridine and 2,6-dibromo-3-nitro-5-chloropyridine instead of 2,6-dibromo-3-chloropyridine.

B. Dressing test

Wheat is artificially infected with the fungus *Tilletia caries*. The wheat is then dressed with 500 ppm of 2,6-dibromo-3-nitro-5-chloropyridine as the active substance and exposed on moist filter paper in Petri dishes. The development of fungus mycelium is assessed after 10 days' incubation at 20° – 24°C. A good action was shown by 2,6-dibromo-3-nitro-5-chloropyridine.

An analogous effect is achieved, if, in the above test, the 500 ppm of 2,6dibromo-3-nitro-5-chloropyridine are replaced by the same quantity of 2,6-dibromo-3-nitropyridine.

What is claimed is:

1. A compound selected from the group consisting of 2,6-dibromo-3-chloropyridine, 2,6-dibromo-3-bromomethyl-5-chloropyridine, 2,6-dibromo-3-bromomethyl-5-nitropyridine, 2,6-dibromonicotinic acid, 2,6-dibromo-5-chloronicotinic acid, 2,6-dibromo-3-trifluoromethylpyridine and 2,6-dibromo-3-chloro-5-aminopyridine.

2. 2,6-Dibromo-3-chloropyridine according to claim 1.

* * * * *